United States Patent [19]

Wenz

[11] 4,326,027

[45] Apr. 20, 1982

[54] ANTIGLOBULIN CONTROL CELLS

[75] Inventor: Barry Wenz, White Plains, N.Y.

[73] Assignee: Albert Einstein College of Medicine of Yeshiva University, Bronx, N.Y.

[21] Appl. No.: 891,019

[22] Filed: Mar. 28, 1978

[51] Int. Cl.$^3$ .................... C12P 21/00; C12N 5/00; G01N 31/00
[52] U.S. Cl. .................................... 435/7; 435/68; 435/240; 424/11; 424/12; 23/230 B
[58] Field of Search .................. 435/7, 177, 240, 174, 435/810; 424/12, 85, 8, 1, 1.5, 11; 23/230 B; 252/408 R

[56] References Cited

U.S. PATENT DOCUMENTS

| | | | |
|---|---|---|---|
| 3,553,310 | 1/1971 | Csizmas et al. | 424/12 |
| 3,914,400 | 10/1975 | Shulman et al. | 424/12 |
| 4,107,287 | 8/1978 | Morton et al. | 435/7 |
| 4,130,634 | 12/1978 | Molinaro et al. | 424/12 |
| 4,166,106 | 8/1979 | Sedlacek et al. | 435/7 |

OTHER PUBLICATIONS

Stratton, et al, "Preparation of Test Cells for the Antiglobulin Test", *Chem. Absts.*, vol. 81, No. 17, pp. 326–327 (1974), abs. No. 102906g.

Ssebabi, "Enzyme Antihuman-globulin Test, Technique to Detect Enzyme Autoantibody", *Chem. Absts.*, vol. 80, No. 23, p. 322, (1974), abs. No. 131445y.

*Primary Examiner*—Thomas G. Wiseman
*Attorney, Agent, or Firm*—Stephen E. Feldman; Marvin Feldman; Steve T. Zelson

[57] ABSTRACT

Antiglobulin control cells are disclosed wherein reagent human red blood cells are coated with univalent antibody fragments. These control cells provide a high degree of specifity in determining the presence of active anti-human sera, which specifity is lacking in conventional Coombs control cells. The evaluation results of the reactivity tests may be performed in the present manner, but the positive hemagglutination provides assurance of anti-human sera activity as opposed to other agglutinating activity, such as protein that might be present.

15 Claims, No Drawings

ANTIGLOBULIN CONTROL CELLS

FIELD OF THE INVENTION

This invention relates to antiglobulin control cells for hematological testing. Specifically this invention relates to antiglobulin controls to provide specifity and assurance in the detection of active anti-human sera.

BACKGROUND OF THE INVENTION

In conventional hematological laboratory analyses, there is widespread use of Coombs control cells to determine the presence of active anti-human sera. The Coombs control cells are used to check the activity of Coombs sera, whereby hemagglutination provided what was generally regarded as a positive asurance of the presence of such activity. However it has been determined that agglutination of red blood cells could be induced by the presence of other materials other than active anti-human sera. Such other materials included the presence of protein molecules, such as albumin. Thus the Coombs control cell while giving positive results, lack the desired specifity to discriminate between active anti-human sera induced agglutination and agglutination induced by the presence of other materials.

It was also reported by Fudenberg et al, in "Serological Studies with Proeolytic Antibody Fragments and 'Hybrid' Andibodies" *Vox Sang.* 9:14(1964), that certain antibody fragments did not agglutinate red cells coated with or containing homologous antigens.

There is now provided by this present invention new reagent control cells which provide the specifity now absent in the Coombs control cells.

It is therefore an object of this invention to provide improved hematological control cells, and the method of preparing same as well as the method of using same.

It is another object of the invention to provide antiglobulin control cells in which the positive result of hemagglutination is positive assurance of the presence of only active anti-human sera.

It is still another object of this invention to provide an accurate assurance of reagent integrity of the present control cells as well as of reagent anti-human sera (e.g. Coombs sera).

It is a further object of this invention to provide improved antiglobulin control cells which may be readily manufactured and extensively employed in several hematological tests.

The aforesaid as well as other objects and advantages will become apparent from a reading of the following specifications and the adjoined claims.

DESCRIPTION OF THE PREFERRED EMODIMENTS

Broadly speaking this present invention comprises reagent human red blood cells having univalent antibodies (3.5S antibody fragments) coated on or bonded to the reagent red blood cells. It has been found that when the 3.5S antibody fragments are coated on reagent human red bloods, the presence of active anti-human sera will cause agglutination, but the presence of other materials that would cause agglutination in the Coombs control cell will not similarly cause agglutination with the control cells of the present invention.

This high degree of specificity is achieved even where the present reagent control cells are highly saturated with 3.5S antibody fragments. This is in marked contrast to the situation present in commercial Coombs control cells wherein a balance must be carefully struck to on one hand provide sufficient saturation to achieve a $+1$ to $+4$ agglutination, while avoiding high saturation which will permit readily induced agglutination by materials other than the active anti-human sera. Table I evidences the present lack of specifity of the Coombs control cells.

TABLE I

| Exp. | No. of tests | Reagents | Purpose and/or simulated Error | Percent of Test Producing Agglutination |
|---|---|---|---|---|
| A | 96 | AGCC. ScC, AHS | Pos. Control | (96/96) 100% |
| B | 105 | AGCC, Alb. | Neg. Control | (57/105) 54% |
| C | 100 | AGCC, NHS | Neg. Control | (58/100) 58% |
| D | 13 | AGCC+0.9 NS | Neg. Control | 0 |
| E | 103 | AGCC+NHS+ScC | Inappropriate addition of antiglobulin control cells following R.T. incubation phase of the indirect antiglobulin test. | (83/103) 81% |
| F | 107 | AGCC, ScC, Alb., NHS | Inappropriate addition of antiglobulin control cells following the high protein phase of the indirect antiglobulin test. | (71/107) 66% |
| G | 102 | AGCC, ScC, NHS, Alb., AHS | Failure to wash adequately prior to the addition of AHS | (60/102) 59% |
| H | 12 | AGCC, ScC, NHS, Alb., AHS-Neut. | Use of an immunologically non-reactive AHS. | (8/12) 67% |

AGCC=Antiglobulin control cells
AHS=Anti-human serum
AHS-Neut.=Neutralized anti-human serum
Alb.=22% Bovine albumin
NHS=Normal human serum
0.9 NS=Normal saline
ScC=Commercial screening cells By the terms "3.5S antibody fragment" it is meant that cleaved portion of an incomplete 7S(IgG) antibody, wherein the disulfide bond cleavage produced 1 Fc and 2 Fab fragments.

The Fab fragments were found to highly saturate the reagent human red blood cells.

In another aspect this present invention comprises the method of preparation of the control cells of present invention. This method starts with obtaining type O+ blood cells. from a panel of known donors, and then testing initially with anti-human serum for antibody activity such as in Lupus. The red blood cells are then washed free of everything but the saline fluid to provide the reagent cells. The next steps are essential aspects of the method and involve proteolytic enzyme digestion of 7S Anti-D-antibodies employing papain to cleave the disulfide bonds so as to form the univalent 3.5S antibody fragments. The fluid containing the fragments is then neutralized with a buffer and then subjected to dialysis to separate out the papain enzyme from the fragments. The isolated fragments are than added to the reagent red cells and a coating or adherence of the univalent 3.5S fragments to the red cell occurs. A high degree of adherence is achieved but the control cells may be substantially diluted to 10:1 or more dilution and yet provide good results. Stabilizers may be added and the control cells stored at 2° to 6° C.

When the afore-described test cells are added to active anti-human sera there is macroscopic agglutination of +1 to +4, as determined per pp: 100-101 the *Technical Methods and Procedures of the American Association of Blood Banks*, 6th edition, American Association of Blood Banks, Washington, D.C. (1974); and wherein the anti-human sera is inactive there will be no such hemagglutination. Furthermore the presence of protein such as albumin in the test mixture will not cause any hemagglutination.

It is to be borne in mind that while the afore-described procedure for preparing the test cells of this invention involves papain enzyme digestion, this present invention contemplates the use of any compound which will cleave the disulfide bond of an incomplete 7S antibody to provide 1 Fc fragment and 2 Fab fragments. Certain enzymes such as pepsin do not cleave the 7S antibody in this manner and are not considered useful pursuant to the present invention.

Anti-human serum (i.e. Coombs serum) is used extensively in direct blood tests (as for Lupus); indirect (screening) blood tests; major-side cross matching and minor-side cross matching. The aforedescribed control cells of the present invention are useful as a replacement for the Coombs control cells now employed to test the activity of the anti-human sera, and in all the above noted tests. The procedures employed in there tests are well known to the hematologist and may be employed with the test cells of the present invention.

It is understood that this invention is not limited to the specific example heretofore described which has been offered merely as illustration and that modifications may be made without departing from the spirit of the invention.

What is claimed is:

1. Hematological control cells comprising human red blood cells immunologically coated with univalent antibody 3.5S Fab fragments of an incomplete antibody wherein the degree of saturation of 3.5S fragments provides a+1 to +4 agglutination in the presence of active anti-human sera.

2. The control cells of claim 1, wherein the presence of protein, there is no hemagglutination.

3. The control cells of claim 1, wherein the control cells are enzyme-free.

4. The control cells of claim 1, wherein the univalent antibody Fab fragments adhere to the reagent red blood cells.

5. Hematological control cells comprising human red blood cells immunologically coated with univalent antibody Fab fragments wherein the univalent antibody Fab fragments are 3.5S fragments of an incomplete antibody, wherein the degree of saturation of 3.5S fragments in the presence of active anti-human sera provides a +1 to +4 agglutination, wherein the red blood cells are O positive.

6. Hematological control cells comprising red blood cells having univalent antibody Fab fragments immunologically adhered thereto wherein the degree of saturation of said fragments provides a+1 to +4 agglutination in the presence of active anti-human sera.

7. A test method for anti-human sera comprising:
   a. cleaving the disulfide bonds of 7S Anti-D-antibodies to provide 3.5S univalent antibody Fab fragments;
   b. immunologically coating human red blood cells with 3.5S univalent antibody Fab fragments;
   c. washing said human red blood cells of step b and
   d. mixing human red blood cells immunologically coated with 3.5S univalent anti-body Fab fragments with a sample containing antihuman sera, whereby an active anti-human sera produce an observable agglutination of the cells; by measuring for the agglutination of the cells.

8. The test method of claim 7, wherein the cleavage is by enzyme digestion.

9. The test method of claim 8, wherein the enzyme is papain.

10. The test method of claim 8, wherein dialysis is used to remove the enzyme from the 3.5S univalent antibody fragments.

11. The test method of claim 7, wherein the degree of saturation of the 3.5S univalent antibody Fab fragment coating provides a +1 to +4 agglutination in the presence of active anti-human sera.

12. The test method of claim 7 further comprising concurrently adding said coated red blood cells to a seperate volume of Coombs serum, whereby the presence of agglutination is positive assurance of the reagent integrity of both the test cells of the present invention as well as the activity of the Coombs serum.

13. The test method of claim 12, wherein the red blood cells are O positive.

14. The test method of claim 13, wherein the agglutination is macroscopic +1 to +4.

15. The test method of claim 7, whereby the presence of protein in the mixture does not agglutinate the red cells but only agglutinates in the presence of active anti-human sera.

* * * * *